United States Patent [19]

Berkowitz

[11] Patent Number: 5,208,220
[45] Date of Patent: May 4, 1993

[54] COMPOSITION AND TREATMENT WITH BIOLOGICALLY ACTIVE PEPTIDES AND ANTIBIOTICS WHICH INHIBIT DNA GYRASE

[75] Inventor: Barry Berkowitz, Ft. Washington, Pa.

[73] Assignee: Magainin Pharmaceuticals, Inc., Plymouth Meeting, Pa.

[21] Appl. No.: 798,253

[22] Filed: Nov. 15, 1991

Related U.S. Application Data

[63] Continuation of Ser. No. 545,356, Jun. 27, 1990, abandoned.

[51] Int. Cl.⁵ .......................... A61K 37/02; C07K 7/10
[52] U.S. Cl. ........................................ 514/13; 514/12; 514/14; 530/324; 530/325; 530/326
[58] Field of Search .............................. 514/12, 13, 14; 530/324, 325, 326

[56] References Cited

U.S. PATENT DOCUMENTS

| | | | |
|---|---|---|---|
| 4,107,298 | 8/1978 | Luning | 530/326 |
| 4,617,149 | 10/1986 | DiMarchi et al. | 530/324 |
| 4,636,489 | 1/1987 | Seemuller et al. | 530/324 |
| 4,659,692 | 4/1987 | Lehrer et al. | 530/324 |
| 4,668,662 | 5/1987 | Tripier | 530/324 |
| 4,791,100 | 12/1988 | Kramer et al. | 530/324 |
| 4,962,277 | 10/1990 | Cuervo et al. | |

FOREIGN PATENT DOCUMENTS 11290 11/1989 PCT Int'l Appl.

OTHER PUBLICATIONS

Gibson, et al., "Novel Peptide Fragments Originating from PGLa and the Caerulein and Xenopsin Precursors from *Xenopus laevis*", *Biol. Chem.*, vol. 261, No. 12 (Apr. 25, 1986).

Giovannini, et al., "Biosynthesis and Degradation of Peptides Derived from *Xenopus laevis* Prohormones,'-'*Biochem J.*, vol. 243, pp. 113–120 (1987).

Viljanen, et al., "Susceptibility of Gram-Negative Bacteria to Polynyzin B Nonapeptide," *Antimicrobial Agents and Chemotherapy*, vol. 25, No. 6, pp. 701–705 (Jun. 1984).

Viljanen, et al., "Susceptibility of Gram-Negative Bacteria to the Synergistic Bactericidal Action of Serum and Polymyxin B Nonapeptide", *Can. J. Microbiol.*, vol. 32, pp. 66–69 (1986).

Vaara, et al., *Antimicrobial Agents and Chemotherapy*, vol. 24, No. 1, pp. 107–113 (Jul. 1983).

Christensen, et al., *Proc. Nat. Acad. Sci.*, vol. 85, pp. 5072–5076 (Jul. 1988).

Primary Examiner—Lester L. Lee
Assistant Examiner—Carol A. Salata
Attorney, Agent, or Firm—Elliot M. Olstein; Raymond J. Lillie

[57] ABSTRACT

A composition comprising at least one biologically active amphiphilic peptide or protein, said peptide or protein being an ion channel-forming peptide or protein, and an antibiotic which inhibits DNA gyrase. The biologically active amphiphilic peptide and the antibiotic which inhibits DNA gyrase may be administered in amounts effective to inhibit growth of a target cell such as a bacterium.

63 Claims, No Drawings

COMPOSITION AND TREATMENT WITH BIOLOGICALLY ACTIVE PEPTIDES AND ANTIBIOTICS WHICH INHIBIT DNA GYRASE

This application is a continuation of Ser. No. 545,356, filed Jun. 27, 1990, and now abandoned.

This invention relates to biologically active peptides and proteins, and more particularly to compositions and uses involving biologically active peptides or proteins and an antibiotic which inhibits DNA gyrase, and in particular quinolone antibiotics such as ciprofloxacin.

In accordance with an aspect of the present invention, there is provided a composition which includes includes at least one biologically active amphiphilic peptide and/or biologically active protein; and an antibiotic which inhibits DNA gyrase.

In accordance with another aspect of the present invention, there is provided a process wherein there is administered to a host at least one biologically active amphiphilic peptide which is an ion channel forming peptide and/or biologically active protein; and an antibiotic which inhibits DNA gyrase.

An ion channel-forming peptide or protein or ionophore is a peptide or protein which increases the permeability for ions across a natural or synthetic lipid membrane. B. Christensen et al. PNAS Vol. 85 Pgs. 5072–76 (July, 1988) describes methodology which indicates whether or not a peptide or protein has ion channel-forming properties and is therefore an ionophore. As used herein an ion channel-forming peptide or ion channel forming protein is a peptide or protein which has ion channel-forming properties as determined by the method of Christensen et al.

An amphiphilic peptide is a peptide which includes both hydrophobic and hydrophilic peptide regions.

In accordance with an aspect of the present invention wherein the biologically active peptide or protein, and an antibiotic which inhibits DNA gyrase are administered to a host, such biologically active peptide or protein and the antibiotic which inhibits DNA gyrase may be administered as a single composition or in separate compositions, and the single or separate compositions may include additional materials, actives and/or inactives, in addition to the peptide and/or protein and antibiotic which inhibits DNA gyrase.

The ion channel-forming peptides employed in the present invention are generally water soluble to a concentration of at least 20 mg/ml at neutral pH in water. In addition, such peptides are non-hemolytic; i.e., they will not rupture blood cells at effective concentrations. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure.

In general, such peptides have at least 16 amino acids, and preferably at least 20 amino acids. In most cases, such peptides do not have in excess of 40 amino acids.

DNA gyrase is an enzyme which is involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin. The following are structural formulae of representative examples of antibiotics which inhibit DNA gyrase.

Nalidixic acid has the following structure:

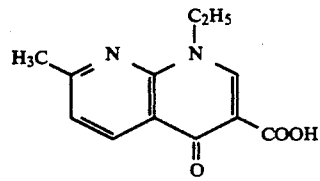

Oxolinic acid has the following structure:

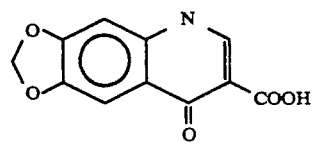

Of the antibiotics which inhibit DNA gyrase which are also quinolone antibiotics, the following are representative structural formulae.

Ciprofloxacin has the following structure:

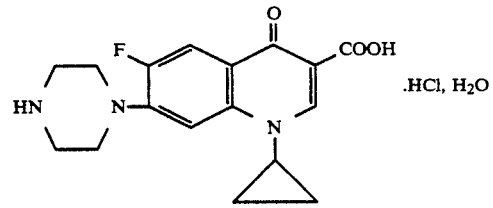

.HCl, H$_2$O

Norfloxacin has the following structure:

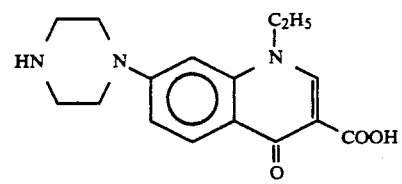

Antibiotics which inhibit DNA gyrase are further described in *Clinical and Infectious Diseases*, W. B. Saunders Co. (1987). In a preferred embodiment, the antibiotic which inhibits DNA gyrase is a quinolone antibiotic, and most preferably, the quinolone antibiotic is ciprofloxacin.

In employing both an ion channel-forming biologically active amphiphilic peptide or an ion channel-forming protein, and an antibiotic which inhibits DNA gyrase, whether administered or prepared in a single composition, or in separate compositions, the peptide or protein and the antibiotic which inhibits DNA gyrase are employed in amounts effective to inhibit and/or prevent and/or destroy the growth of a target cell. In effect, the quinolone antibiotic potentiates the action of the peptide or protein, and the peptide or protein potentiates the action of the antibiotic which inhibits DNA gyrase. The term "potentiate," as employed herein, means that the amount of antibiotic which inhibits DNA gyrase is effective to reduce the minimum effective concentration of the peptide or protein for inhibiting growth of a target cell and the amount of peptide or protein is effective to reduce the minimum effective concentration of the antibiotic which inhibits DNA gyrase for inhibiting growth of a target cell.

In general, the peptide or protein is administered topically at a concentration of from 0.05% to 10%. When administered systemically, the peptide or protein is employed to provide peptide or protein dosages of from 1 mg to 500 mg per kilogram of host weight.

The antibiotic which inhibits DNA gyrase, in general, is used topically at a concentration of from 0.05% to 10%. When used systemically, the antibiotic which inhibits DNA gyrase is generally employed in an amount of from 1.25 to 45 mg per kilogram of host weight per day.

The use of a combination of peptide or protein and antibiotic which inhibits DNA gyrase, in accordance with the present invention is effective as an antibiotic, and may be employed to inhibit, prevent or destroy the growth or proliferation of microbes, such as bacteria.

The compositions have a broad range of potent antibiotic activity against a plurality of microorganisms, including Gram-positive and Gram-negative bacteria. Such compositions may be employed for treating or controlling microbial infection caused by organisms which are sensitive to such compositions. The treatment may comprise administering to a host organism or tissues acceptable to or affiliated with a microbial infection an anti-microbial amount of such peptide or protein and antibiotic which inhibits DNA gyrase.

The compositions may also be used as preservatives or sterilants for materials susceptible to microbial contamination.

The compositions of the present invention may also be used in the treatment of external burns and to treat and/or prevent skin and burn infections. In particular, the compositions may be used to treat skin and burn infections caused by organisms such as, but not limited to, P. aeruginosa and S. aureus.

Such compositions may also be used in the prevention or treatment of eye infections. Such infections may be caused by bacteria such as, but not limited to, P. aeruginosa, S. auerus, and N. gonorrhoeae.

In accordance with a preferred embodiment, the peptide used in conjunction with the antibiotic which inhibits DNA gyrase is a basic (positively charged) polypeptide having at least sixteen amino acids wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acid, with such groups of two hydrophilic amino acids being spaced from each other by at least one amino acid other than a hydrophilic amino acid (preferably at least two amino acids) and generally no greater than four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids. Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of Ala, Cys, Phe, Gly, Ile, Leu, Met, Val, Trp, and Tyr. The neutral hydrophilic amino acids may be selected from the class consisting of Asn, Gln, Ser, and Thr. The basic hydrophilic amino acids may be selected from the class consisting of Lys, Arg, His and ornithine (O).

Each of the groups of four amino acids may be of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different. In a preferred embodiment, the polypeptide chain may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary provided that in each group of the at least four groups of amino acids there are two hydrophobic and two hydrophilic amino acids as hereinabove noted.

Thus, in a preferred embodiment, the biologically active polypeptide comprises a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic amino acids, one of C or D is a basic hydrophilic amino acid, and the other of C or D is basic or neutral hydrophilic amino acid. The resulting polypeptide chain, therefore, may have one of the following sequences:

$(X_1)_a(A-B-C-D)_n(Y_1)_b$
$(X_2)_a(B-C-D-A)_n(Y_2)_b$
$(X_3)_a(C-D-A-B)_n(Y_3)_b$
$(X_4)_a(D-A-B-C)_n(Y_4)_b$ wherein $X_1$ is D; C-D- or B-C-D-, $Y_1$ is -A or -A-B or -A-B-C $X_2$ is A-, D-A- or C-D-A-
$Y_2$ is -B, -B-C or B-C-D $Y_3$ is B-, A-B, D-A-B-
$Y_3$ is -C, -C-D, -C-D-A
$X_4$ is C-, B-C-, A-B-C-
$Y_4$ is -D, -D-A, -D-A-B
a is 0 or 1; b is 0 or 1
and n is at least 4.

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and do not adversely affect the folding characteristics of the chain to that which is significantly different from one in which the hereinabove noted group of four amino acids are not spaced from each other.

As representative examples of peptides in accordance with the present invention, there may be mentioned.

I
Ala—Phe—Ser—Lys—Ala—Phe—Ser—Lys—Ala—Phe—Ser—Lys—Ala—Phe—Ser—Lys—Ala—Phe—Ser—Lys

II
Ala—Phe—Ser—Lys—Ala—Phe—Ser—Lys—Ala—Phe—Ser—Lys—Ala—Phe—Ser—Lys—Ala—Phe—Ser—Lys—Ala—Phe—Ser—Lys.

III
Phe—Ser—Lys—Ala—Phe—Ser—Lys—Ala—Phe—Ser—Lys—Ala—Phe—Ser—Lys—Ala—

IV
Ser—Lys—Ala—Phe—Ser—Lys—Ala—Phe—Ser—Lys—Ala—Phe—Ser—Lys—Ala—Phe—Ser—Lys—Ala—Phe—

V
Lys—Ala—Phe—Ser—Lys—Ala—Phe—Ser—Lys—Ala—Phe—Ser—Lys—Ala—Phe—Ser

The peptide, may have amino acids extending from either end of the chain. For example, the chains may have a Ser-Lys sequence before the "Ala" end, and/or an Ala-Phe sequence after the "Lys" end. Other amino acid sequences may also be attached to the "Ala" and-/or the "lys" end.

Similarly, in any polypeptide chain having at least four groups of amino acids of the sequence as described above, the chain may have, for example, a C-D sequence before the first A-B-C-D group. Also other amino acid sequences may be attached to the "A" and-/or the "D" end of one of these polypeptide chains. Also there may be amino acids in the chain which space one or more groups of the hereinabove noted four amino acids from each other.

The peptides may be produced by known techniques and obtained in substantially pure form. For example, the peptides may be synthesized on an automatic synthesizer. Journal of American Chemical Society, Vol. 85 Pages 2149-54(1963). It is also possible to produce such peptides by genetic engineering techniques.

In accordance with another preferred embodiment, the peptide employed in conjunction with an antibiotic which inhibits DNA gyrase may be a magainin peptide.

A magainin peptide is either a magainin such as magainin I, II or III or an analogue or derivative thereof. The magainin peptides preferably include the following basic peptide structure $X_{12}$ $R_{11}$—$R_{11}$—$R_{12}$—$R_{13}$—$R_{11}$—$R_{14}$—$R_{12}$—$R_{11}$—$R_{14}$—$R_{12}$—$R_{11}$—$R_{11}$—$R_{11}$—$R_{14a}$—$(R_{15})_n$—$R_{14a}$—$R_{14}$— wherein $R_{11}$ is a hydrophobic amino acid, $R_{12}$ is a basic hydrophilic amino acid; $R_{13}$ is a hydrophobic, neutral hydrophilic, or basic hydrophilic amino acid; $R_{14}$ and $R_{14a}$ are hydrophobic or basic hydrophilic amino acids; $R_{15}$ is glutamic acid or aspartic acid, or a hydrophobic or a basic hydrophilic amino acid, and n is 0 or 1. In a preferred embodiment, $R_{13}$ is a hydrophobic or neutral hydrophilic amino acid, $R_{14a}$ is a hydrophobic amino acid, and $R_{15}$ is glutamic acid or aspartic acid.

Thus, for example, a magainin peptide may include the following structure:

$$-Y_{12}-X_{12}-$$

where $X_{12}$ is the hereinabove described basic peptide structure and $Y_{12}$ is (i) $R_{12}$ (ii) $R_{14a}$—$R_{12}$ (iii) $R_{11}$—$R_{14a}$—$R_{12}$ (iv) $R_{14}$—$R_{11}$—$R_{14a}$—$R_{12}$ where $R_{11}$, $R_{12}$, $R_{14}$ and $R_{14a}$ are as previously defined.

A magainin peptide may also have the following structure:

$$-X_{12}-Z_{12}-$$

wherein $X_{12}$ is as previously defined and $Z_{12}$ is:

(i) $R_{16}$ and $R_{16}$ is a basic hydrophilic amino acid or asparagine or glutamine.

(ii) $R_{16}$—$R_{17}$ where $R_{17}$ is a neutral hydrophilic amino acid, a hydrophobic amino acid, or a basic hydrophilic amino acid. Preferably, $R_{17}$ is a neutral hydrophilic amino acid.

A magainin peptide may also have the following structure:

$$(Y_{12})_a - X_{12} - (Z_{12})_b$$

where $X_{12}$, $Y_{12}$ and $Z_{12}$ are as previously defined and a is 0 or 1 and b is 0 or 1.

The magainin peptides may also include the following basic peptide structure $X_{13}$:

—$R_{14}$—$R_{11}$—$R_{14a}$—$R_{12}$—$R_{11}$—$R_{11}$—$R_{12}$—$R_{13}$—$R_{11}$—$R_{14}$—$R_{12}$—$R_{11}$—$R_{11}$—$R_{12}$—, wherein $R_{11}$, $R_{12}$, $R_{13}$, $R_{14}$, and $R_{14a}$ are amino acids as hereinabove described.

The magainin peptide may also include the following structure $X_{13}$—$Z_{13}$; wherein $X_{13}$ is the hereinabove described basic peptide structure and $Z_{13}$ is $(R_{11})_n$—$(R_{11})_n$—$(R_{11})_n$—$(R_{14a})_n$—$(R_{15})_n$—$(R_{14a})_n$—$(R_{14})_n$—$(R_{16})_n$— $(R_{17})_n$ wherein $R_{11}$, $R_{14}$, $R_{14a}$, $R_{15}$, $R_{16}$, and $R_{17}$ are as hereinabove described, and n is 0 or 1, and each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequence (expressed as a single letter code) as well as appropriate analogues and derivatives thereof:
(a) (NH$_2$) GIGKFLHSAGKFGKAFVGEIMKS(OH) or (NH$_2$) (Magainin I)
(b) (NH$_2$) GIGKFLHSAKKFGKAFVGEIMNS(OH) or (NH$_2$) (Magainin II)
(c) (NH$_2$) GIGKFLHSAKKFGKAFVGEIMN(OH) or (NH$_2$) (Magainin III)

The following are examples of peptide derivatives or analogs of the basic structure:
(d) (NH$_2$) IGKFLHSAKKFGKAFVGEIMNS(OH) or (NH$_2$)
(e) (NH$_2$) GKFLHSAKKFGKAFVGEIMNS(OH) or (NH$_2$)
(f) (NH$_2$) KFLHSAKKFGKAFVGEIMNS(OH) or (NH$_2$)

Magainin peptides are described in *Proc. Natl. Acad Sci.* Vol. 84 pp. 5449-53 (Aug. 87). The term "magainin peptides" as used herein refers to the basic magainin structure as well as derivatives and analogs thereof, including but not limited to the representative derivatives or analogs.

In accordance with a further embodiment, the peptide employed in conjunction with an antibiotic which inhibits DNA gyrase may be a PGLa peptide or an XPF peptide.

A PGLa peptide is either PGLa or an analogue or derivative thereof. The PGLa peptides preferably include the following basic peptide structure $X_{14}$:

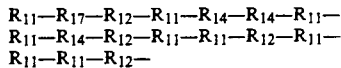

where $R_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl end.

Thus, for example, a PGLa peptide may have the following structure:

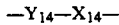

where $X_{14}$ is as previously defined and $Y_{14}$ is
(i) $R_{11}$;
(ii) $R_{14}$—$R_{11}$
where $R_{11}$ and $R_{14}$ are as previously defined.

For example, a PGLa peptide may also have the following structure:

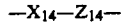

where $X_{14}$ is as previously defined; and $Z_{14}$ is:
(i) $R_{11}$; or
(ii) $R_{11}$—$R_{11}$
where $R_{11}$ is as previously defined.

A PGLa peptide may also have the following structure:

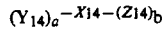

where $X_{14}$; $Y_{14}$ and $Z_{14}$ are as previously defined, a is 0 or 1 and b is 0 or 1.

An XPF peptide is either XPF or an analogue or derivative thereof. The XPF peptides preferably include the following basic peptide structure $X_{16}$:

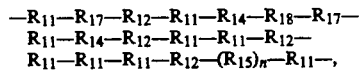

$R_{11}$, $R_{12}$, $R_{14}$, $R_{15}$ and $R_{17}$ are as previously defined and $R_{18}$ is glutamine or asparagine or a basic hydrophilic, or hydrophobic amino acid and, n is O or 1.

The XPF peptides generally include at least nineteen amino acids and may include up to forty amino acids. Accordingly, the hereinabove described basic peptide structure of XPF may include additional amino acids at the amino end, or at the carboxyl end or at both the amino and carboxyl ends.

Thus, for example, an XPF peptide may include the following structure:

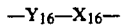

where $X_{16}$ is as previously defined and $Y_{16}$ is
(i) $R_{11}$ or
(ii) $R_{14}$—$R_{11}$
where $R_{11}$ and $R_{14}$ are as previously defined.

An XPF peptide may include the following structure:

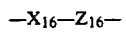

where $X_{16}$ is as previously defined and $Z_{16}$ is (i) $R_{11}$; or
(ii) $R_{11}$—$R_{18}$; or
(iii) $R_{11}$—$R_{18}$—Proline; or
(iv) $R_{11}$—$R_{18}$—Proline—$R_{12}$ An XPF peptide may also have the following structure:

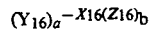

where $X_{16}$, $Y_{16}$ and $Z_{16}$ are as previously defined: a is 0 or 1 and b is 0 or 1.

Preferred are XPF or PGLa peptides, which are characterized by the following primary amino acid sequence(single letter amino acid code):
PGLa: GMASKAGAIAGKIAKVALKAL (NH$_2$)
XPF: GWASKIGQTLGKIAKVGLKELIQPK A review of XPF and PGLa can be found in Hoffman et al, *EMBO J.* 2:711-714, 1983; Andreu et al, *J. Biochem.* 149:531-535, 1985; Gibson et al *J. Biol. Chem.* 261:5341-5349, 1986; and Giovannini et al, *Biochem J.* 243:113-120, 1987.

In accordance with yet another embodiment, the peptide employed in conjunction with an antibiotic which inhibits DNA gyrase may be a CPF peptide or appropriate analogue or derivative thereof.

CPF peptides as well as analogues and derivatives thereof are herein sometimes referred to collectively as CPF peptides.

The CPF peptide is preferably one which includes the following peptide structure $X_{30}$:

$$-R_{21}-R_{21}-R_{22}-R_{22}-R_{21}-R_{21}-R_{23}-R_{21}-$$
$$-R_{21}-R_{21}-R_{23}-R_{21}-R_{21}-R_{24}-R_{25}-R_{21}-$$

wherein $R_{21}$ is a hydrophobic amino acid;

$R_{22}$ is a hydrophobic amino acid or a basic hydrophilic amino acid;

$R_{23}$ is a basic hydrophilic amino acid; and $R_{24}$ is a hydrophobic or neutral hydrophilic amino acid; and $R_{25}$ is a basic or neutral hydrophilic amino acid.

The hereinabove basic structure is hereinafter symbolically indicated as $X_{30}$.

The hydrophobic amino acids are Ala, Cys, Phe, Gly, Ile, Leu, Met, Val, Trp, and Tyr.

The neutral hydrophilic amino acids are Asn, Gln, Ser, and Thr.

The basic hydrophilic amino acids are Lys, Arg, His, and ornithine.

The CPF peptide may include only the hereinabove noted amino acids or may include additional amino acids at the amino end or carboxyl end or both the amino and carboxyl end. In general, the peptide does not include more than 40 amino acids.

The CPF peptides including the above basic peptide structure may have from 1 to 4 additional amino acids at the amino end. Accordingly, such preferred peptides may be represented by the structural formula:

$$Y_{30}-X_{30}-$$

wherein $X_{30}$ is the hereinabove described basic peptide structure and $Y_{30}$ is (i) $R_{25}-$, or
(ii) $R_{22}-R_{25}$; or
(iii) $R_{21}-R_{22}-R_{25}$; or
(iv) $R_{22}-R_{21}-R_{22}-R_{25}$; preferably
    Glycine $-R_{21}-R_{22}-R_{25}-$ wherein $R_{21}$, $R_{22}$, and $R_{25}$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

$$-X_{30}-Z_{30}$$

wherein $X_{30}$ is the hereinabove defined basic peptide structure and $Z_{30}$ is (i) $R_{21}-$,
(ii) $R_{21}-R_{21}-$;
(iii) $R_{21}-R_{21}-R_{24}$;
(iv) $R_{21}-R_{21}-R_{24}-R_{24}$;
(v) $R_{21}-R_{21}-R_{24}-R_{24}-R_{26}$;
(vi) $R_{21}-R_{21}-R_{24}-R_{24}-R_{26}-$Gln; or
(vii) $R_{21}-R_{21}-R_{24}-R_{24}-R_{26}-$Gln$-$Gln, wherein $R_{21}$ and $R_{24}$ are as previously defined, and $R_{26}$ is proline or a hydrophobic amino acid.

Preferred peptides may be represented by the following structural formula:

$$(Y_{30})_a - X_{30} - (Z_{30})_b$$

wherein $X_{30}$, $Y_{30}$ and $Z_{30}$ are as previously defined and $a$ is 0 or 1 and $b$ is 0 or 1.

Representative examples of CPF peptides which are useful in the present invention some of which have been described in the literature and comprise the following sequences (single letter amino acid code):

(1) GFGSFLGLALKAALKIGANALGGAPQQ
(2) GLASFLGKALKAGLKIGAHLLGGAPQQ
(3) GLASLLGKALKAGLKIGTHFLGGAPQQ
(4) GLASLLGKALKATLKIGTHFLGGAPQQ
(5) GFASFLGKALKAALKIGANMLGGTPQQ
(6) GFGSFLGKALKAALKIGANALGGAPQQ
(7) GFGSFLGKALKAALKIGANALGGSPQQ
(8) GFASFLGKALKAALKIGANLLGGTPQQ

A review of the CPF peptides can be found in Richter, K., Egger, R., and Kreil (1986) J. Biol. Chem. 261, 3676-3680; Wakabayashi, T. Kato, H., and Tachibaba, S. (1985) Nucleic Acids Research 13, 1817-1828; Gibson, B. W., Poulter, L., Williams, D. H., and Maggio, J. E. (1986) J. Biol. Chem. 261, 5341-5349.

CPF peptides which may be employed in the present invention are represented by the following (single letter amino acid code):

G12S3LG4ALKA5LKIG678LGG9(10)QQ

Where:
  1 = F, L
  2 = G, A
  3 = F, L
  4 = K, L
  5 = A, G, T
  6 = A, T
  7 = H, N
  8 = A, M, F, L
  9 = A, S, T
  10 = P, L The numbered amino acids may be employed as described in any combination to provide either a basic CPF peptide structure or an analogue or derivative. The term CPF peptide includes the basic peptide structure as well as analogs or derivatives thereof.

In accordance with still another embodiment, the biologically active peptide may include the following basic strucutre $X_{40}$:

$[R_{41}-R_{42}-R_{42}-R_{43}-R_{41}-R_{42}-R_{42}]_n$, wherein $R_{41}$ is a basic hydrophilic amino acid, $R_{42}$ is a hydrophobic amino acid, $R_{43}$ is a neutral hydrophilic or hydrophobic amino acid, and n is from 2 to 5.

In one embodiment, such peptide may include the following structure:

$Y_{40}-X_{40}$, wherein $X_{40}$ is as hereinabove described, and $Y_{40}$ is:

(i) $R_{42}$;
(ii) $R_{42}-R_{42}$;
(iii) $R_{41}-R_{42}-R_{42}$;
(iv) $R_{43}-R_{41}-R_{42}-R_{42}$;
(v) $R_{42}-R_{43}-R_{41}-R_{42}-R_{42}$; or
(vi) $R_{42}-R_{42}-R_{43}-R_{41}-R_{42}-R_{42}$, wherein $R_{41}$, $R_{42}$, and $R_{43}$ are as hereinabove described In accordance with another embodiment, such peptide may include the following structure:

$X_{40}-Z_{40}$, wherein $X_{40}$ is as hereinabove described, and $Z_{40}$ is:

(i) $R_{41}$;
(ii) $R_{41}-R_{42}$;
(iii) $R_{41}-R_{42}-R_{42}$;
(iv) $R_{41}-R_{42}-R_{42}-R_{43}$;

(v) $R_{41}$—$R_{42}$—$R_{42}$—$R_{43}R_{41}$; or (vi) $R_{41}$—$R_{42}$—$R_{42}$—$R_{43}$—$R_{41}$—$R_{42}$.

In accordance another embodiment, such peptide may include the following structure:

$(Y_{40})_a$—$X_{40}$—$(Z_{40})_b$, wherein Y and Z are as previously defined, a is 0 or 1, and b is 0 or 1.

In one embodiment, n is 3, and most preferably the peptide is of the following structure as indicated by the single letter amino acid code:

[KIAGKIA]$_3$.

In another embodiment, n is 2, and the peptide preferably is of the following structure as indicated by the single letter amino acid code:

KIA(KIAGKIA)$_2$KIAG.

In accordance with yet another embodiment, the biologically active amphiphilic peptide may be a biologically active amphiphilic peptide including the following basic structure $X_{50}$:

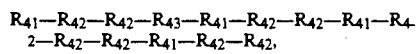

wherein $R_{41}$, $R_{42}$ and $R_{43}$ are as hereinabove described.

In accordance with one embodiment, such peptide may include the following structure:

$Y_{50}$—$X_{50}$, wherein $X_{50}$ is as hereinabove described, and $Y_{50}$ is:

(i) $R_{42}$;
(ii) $R_{42}$—$R_{42}$;
(iii) $R_{41}$—$R_{42}$—$R_{42}$;
(iv) $R_{43}$—$R_{41}$—$R_{42}$—$R_{42}$;
(v) $R_{42}$—$R_{43}$—$R_{41}$—$R_{42}$—$R_{42}$;
(vi) $R_{42}$—$R_{42}$—$R_{43}$—$R_{41}$—$R_{42}$—$R_{42}$, or
(vii) $R_{41}$—$R_{42}$—$R_{42}$—$R_{43}$—$R_{41}$—$R_{42}$—$R_{42}$, wherein $R_{41}$, $R_{42}$ and $R_{43}$ are as hereinabove described.

In accordance with another embodiment, such peptide may include the following structure:

$X_{50}$—$Z_{50}$, wherein $X_{50}$ is as hereinabove described and $Z_{50}$ is:

(i) $R_{41}$;
(ii) $R_{41}$—$R_{42}$;
(iii) $R_{41}$—$R_{42}$—$R_{42}$;
(iv) $R_{41}$—$R_{42}$—$R_{42}$—$R_{43}$;
(v) $R_{41}$—$R_{42}$—$R_{42}$—$R_{43}$—$R_{41}$;
(vi) $R_{41}$—$R_{42}$—$R_{42}$—$R_{43}$—$R_{41}$—$R_{42}$; or
(vii) $R_{41}$—$R_{42}$—$R_{42}$—$R_{43}$—$R_{41}$—$R_{42}$—$R_{42}$, wherein $R_{41}$, $R_{42}$ and $R_{43}$ are as hereinabove described.

In accordance with yet another embodiment the peptide may include the following structure:

$(Y_{50})_a$—$X_{50}$—$(Z_{50})_b$, wherein X and Y are as previously defined, a is 0 or 1, and b is 0 or 1. In one embodiment, the peptide is of the following structural formula as indicated by the single letter amino acid code:

KLASKAGKIAGKIAKVALKAL.

In another embodiment, the peptide is of the following structural formula as indicated by the single letter amino acid code:

KIAGKIAKIAGOIAKIAGKIA.

In still another embodiment, the peptide employed in conjunction with an antibiotic which inhibits DNA gyrase is a cecropin. The cecropins and analogs and derivatives thereof are described in Ann. Rev. Microbiol 1987 Vol. 41 pages 103–26, in particular p. 108 and Christensen et al PNAS Vol. 85 p. 5072–76, which are hereby incorporated by reference.

The term cecropins includes the basic structure as well as analogues and derivatives.

In yet another embodiment, the peptide employed in conjunction with an antibiotic which inhibits DNA gyrase is a sarcotoxin. The sarcotoxins and analogs and derivatives thereof are described in Molecular Entomology pages 369–78 in particular p. 375 Alan R. Liss Inc. (1987), which is hereby incorporated by reference.

The term sarcotoxin includes the basic materials as well as analogues and derivatives.

It is also contemplated that within the scope of the present invention, that each of the amino acid residues of the biologically active amphiphilic peptide structures hereinabove described is a D-amino acid residue or a glycine residue.

In another embodiment, an ion channel-forming protein may be used in conjunction with an antibiotic which inhibits DNA gyrase. Ion channel-forming proteins which may be employed include defensins, also known as human neutrophil antimicrobial peptides (HNP), major basic protein (MBP) or eosinophils, bactericidal permeability-increasing protein (BPI), and a pore-forming cytotoxin called variously perforin, cytolysin, or pore-forming protein. Defensins are described in Selsted, et al., *J. Clin. Invest.*, Vol. 76, pgs. 1436–1439 (1985). MBP proteins are described in Wasmoen, et al., *J. Biol. Chem.*, Vol. 263, pgs 12559–12563. (1988). BPI proteins are described in Ooi, et al, *J. Biol. Chem.*, Vol. 262, pgs. 14891–14894 (1987). Perforin is described in Henkart, et al., *J. Exp. Med.*, 160: 75 (1984), and in Podack, et al., *J. Exp. Med.*, 160:695 (1984). The above articles are hereby incorporated by reference.

The term ion channel-forming proteins includes the basic structures of the ion-forming proteins as well as analogues and derivatives.

The present invention will be further described with respect to the following example; however, the scope of the invention is not to be limited thereby.

EXAMPLE 1

Approximately 1–5×10$^5$ colony forming units (CFU's) of *P.aeruginosa* strain 27853 or of *P.aeruginosa* strain 107 (which is gentamicin - resistant) dispersed in 100 ul of trypticase soy broth (TSB) were added to each of a series of test wells. Either Peptide 1, Peptide 2, or Peptide 3 was added to each test well in increasing amounts from 0.25 to 256 μg/ml in absence of or in the presence of 20% of the minimal inhibitory concentration (MIC) of ciprofloxacin. For purposes of this example, Peptide 1 is amide-terminated Magainin II, Peptide 2 is of the following structural formula:

[KIAGKIA]$_3$;

and Peptide 3 is of the following structural formula:

KLASKAGKIAGKIAKVALKAL.

The MIC of ciprofloxacin alone against *P.aeruginosa* strain 27853 was 1 μg/ml, and against *P.aeruginosa* strain 107 was 2 μg/ml. The MIC values for Peptides 1, 2 and 3, either alone or in combination with 20% of the MIC of ciprofloxacin are given in Table I below.

TABLE I

|   | | MIC (μg/ml) P. aeruginosa strain | |
|---|---|---|---|
|   | | 27853 | 107 |
| 1. | Peptide 1 alone | >32 | >32 |
| 2. | Peptide 1 plus 20% MIC of ciprofloxacin | 32 | 32 |
| 3. | Peptide 2 alone | 32 | 32 |
| 4. | Peptide 2 plus 20% MIC of ciprofloxacin | 16 | 16 |
| 5. | Peptide 3 alone | 16 | 32 |
| 6. | Peptide 3 plus 20% MIC of ciprofloxacin | 8 | 8 |

EXAMPLE 2

For Examples 2 and 4, microorganisms employed in the assays were grown according to the procedure described in Stutman, et al., *Antimicrobial Agents in Chemotherapy*, Vol. 34, July 1990.

In Examples 2 through 4, organisms were subcultured on agar plates, and then grown in trypticase soy broth (TSB), or Mueller-Hinton broth. The final assays were then conducted in microtiter plates containing Mueller-Hinton broth $10^5$ organisms were added to each well.

The minimal inhibitory concentrations (MIC's) of ciprofloxacin alone, of Peptide 1, as hereinabove described in Example 1, alone, of ciprofloxacin when Peptide 1 was added (ciprofloxacin+Peptide 1), and of Peptide 1 when ciprofloxacin was added, (Peptide 1+ciprofloxacin) were tested against various isolates of strain MR-PSA (multiply resistant *Pseudomes aerugi-nosa*) *Pseudomonas aeruginosa*. The second compound (or "+" compound) dose to establish synergy was the lowest dose of the synergizing drug which alone lacked antibacterial effect and was at least a 50% lower dose than the MIC for the synergizing agent alone. The results are given below in Table 2.

TABLE 2

| Isolate | Ciprofloxacin Alone | MIC (μg/ml) Ciprofloxacin + Peptide 1 | Peptide 1 Alone | Peptide 1 + Ciprofloxacin |
|---|---|---|---|---|
| 1 | ≦0.5 | ≦0.5 | 32 | 8 |
| 2 | ≦0.5 | N/A | >256 | N/A |
| 3 | 0.25 | ≦0.25 | 32 | 8 |
| 4 | 1.0 | ≦0.5 | 256 | 64 |

The minimal inhibitory concentrations, (MIC's), according to the procedure of Example 2, were tested against various isolates of strain MR-PSA, of *Pseudomonas aeruginosa*, except that Peptide 4 replaces Peptide 1. Peptide 4 has the following structural formula:
GIGKFLKSAKKFGKAFVKIMNS. The results are given below in Table 3.

TABLE 3

| Isolate # | Ciprofloxacin Alone | MIC (μg/ml) Ciprofloxacin + Peptide 4 | Peptide 4 Alone | Peptide 4 + ciprofloxacin |
|---|---|---|---|---|
| 1 | 2 | ≦0.5 | 32 | 8 |
| 2 | 0.25 | 0.25 | 4 | 4 |
| 3 | 0.25 | 0.25 | 8 | 8 |
| 4 | 0.063 | 0.25 | 8 | 8 |
| 5 | 0.25 | 0.063 | 8 | 4 |
| 6 | 4 | ≦0.5 | 32 | 8 |
| 7 | 0.125 | 0.25 | 16 | 16 |
| 8 | 0.5 | 0.5 | 16 | 16 |
| 9 | 2 | ≦0.5 | 32 | 16 |
| 10 | 0.25 | 0.25 | 8 | 8 |
| 11 | 1 | ≦0.125 | 64 | 0.5 |
| 12 | 2 | ≦0.5 | 32 | 8 |

EXAMPLE 4

The minimal inhibitory concentrations (MIC's) of Peptide 4 and ciprofloxacin, either alone or in combination with each other, according to the procedure described in Example 3, were tested against various isolates of *Staphylococcus aureus*. The results are given in Table 4 below.

TABLE 4

| Isolate # | Ciprofloxacin Alone | MIC (μg/ml) Ciprofloxacin + Peptide 4 | Peptide 4 Alone | Peptide 4 + Ciprofloxacin |
|---|---|---|---|---|
| 1 | 1 | 0.125 | 32 | 8 |
| 2 | 0.25 | 0.25 | 16 | 16 |
| 3 | 0.5 | 0.125 | 32 | 2 |
| 4 | >0.25 | 0.063 | 64 | 32 |

The peptide or protein and antibiotic which inhibits DNA gyrase, as hereinabove described, may be employed for treating a wide variety of hosts. In accordance with a preferred embodiment, a host is an animal, and such animal may be a human or non-human animal. The peptide or protein and the antibiotic which inhibits DNA gyrase may be employed together in a single composition, or in separate compositions. Moreover, the antibiotic which inhibits DNA gyrase and the peptide or protein may be delivered or administered in different forms, for example, the antibiotic which inhibits DNA gyrase may be administered systemically, while the peptide or protein may be administered topically.

The peptide or protein and/or antibiotic which inhibits DNA gyrase may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as liquid, solid, semi-solid, injectable solution, tablet, ointment, lotion, paste, capsule, or the like. The peptide or protein and/or antibiotic which inhibits DNA gyrase may also be used in combination with adjuvants, protease inhibitors, or compatible drugs where such a combination is seen to be desirable or advantageous in controlling infection caused by harmful microorganisms, in particular bacteria.

The peptide(s) or protein(s) of the present invention may be administered to a host; in particular an animal, in an effective anti-microbial, in particular in an anti-bacterial amount, in conjunction with an antibiotic which inhibits DNA gyrase, for potentiating the activity of the peptide or protein.

As representative examples of administering the peptide or protein and antibiotic which inhibits DNA gyrase for topical or local administration, the peptide could be administered in an amount of up to about 1% weight to weight and the antibiotic which inhibits DNA gyrase delivered in an amount of about 50 mM (about 0.1%). Alternatively, the antibiotic which inhibits DNA gyrase could be administered topically in conjunction with systemic administration of the peptide and/or protein. For example, the peptide or protein may be administered IV or IP to achieve a serum dose of 100 microorganisms per milliliter (10 milligrams per kilogram) in conjunction with a topical dose of antibiotic which inhibits DNA gyrase of from about 4 μg/ml to about 100 μg/ml.

Numerous modifications and variations of the present invention are possible in light of the above teachings and, therefore, within the scope of the appended claims, the invention may be practiced other than as particularly described.

What is claimed is:

1. A process of inhibiting growth of a microbe in a host, comprising:
   administering to a host at least one biologically active amphiphilic peptide and/or biologically active protein, said biologically active peptide or protein being an ion channel-forming peptide or protein; and
   an antibiotic which inhibits DNA gyrase, said components being administered in a combined amount effective to inhibit growth of a microbe in a host.

2. The process of claim 1 wherein the peptide is a magainin peptide.

3. The process of claim 1 wherein the peptide includes the following basic structure $X_{40}$:

$$[R_{41}-R_{42}-R_{42}-R_{43}-R_{41}-R_{42}-R_{42}]_n,$$

wherein $R_{41}$ is a basic hydrophilic amino acid, $R_{42}$ is a hydrophobic amino acid, $R_{43}$ is a neutral hydrophilic or hydrophobic amino acid, and n is from 2 to 5.

4. The process of claim 1 wherein the peptide includes the following basic structure $X_{50}$:

$R_{41}-R_{42}-R_{42}-R_{43}-R_{41}-R_{42}-R_{42}-R_{41}-R_{42}-R_{42}-R_{41}-R_{42}-R_{42},$ wherein $R_{41}$ is a basic hydrophilic amino acid, $R_{42}$ is a hydrophobic amino acid, and $R_{43}$ is a neutral hydrophilic or hydrophobic amino acid.

5. The process of claim 1 wherein said antibiotic which inhibits DNA gyrase is a quinolone antibiotic.

6. The process of claim 5 wherein said quinolone antibiotic is ciprofloxacin.

7. The process of claim 1 wherein said antibiotic which inhibits DNA gyrase is nalidixic acid.

8. The process of claim 1 wherein said antibiotic which inhibits DNA gyrase is oxolinic acid.

9. The process of claim 1 wherein said antibiotic which inhibits DNA gyrase is cinoxacin.

10. A composition, comprising:
    (a) at least one biologically active amphiphilic peptide and/or biologically active protein, said peptide or protein being an ion channel-forming peptide or protein;
    (b) an antibiotic which inhibits DNA gyrase; and
    (c) an acceptable pharmaceutical carrier, wherein said components (a) and (b) are present in a combined amount effective to inhibit growth of a microbe.

11. The composition of claim 10 wherein the peptide is a magainin peptide.

12. The composition of claim 10 wherein the peptide includes the following basic structure $X_{40}$:

$$[R_{41}-R_{42}-R_{42}-R_{43}-R_{41}-R_{42}-R_{42}]_n$$

wherein $R_{41}$ is a basic hydrophilic amino acid, $R_{42}$ is a hydrophobic amino acid, $R_{43}$ is a neutral hydrophilic or hydrophobic amino acid, and n is from 2 to 5.

13. The composition of claim 10 wherein the peptide inlcudes the following basic structure $X_{50}$:

$R_{41}-R_{42}-R_{42}-R_{43}-R_{41}-R_{42}-R_{42}-R_{41}-R_{42}-R_{42}-R_{41}-R_{42}-R_{42},$ wherein $R_{41}$ is a basic hydrophilic amino acid, $R_{42}$ is a hydrophobic amino acid and $R_{43}$ is a neutral hydrophilic or hydrophobic amino acid.

14. The composition of claim 10 wherein said antibiotic which inhibits DNA gyrase is a quinolone antibiotic.

15. The composition of claim 14 wherein said quinolone antibiotic is ciprofloxacin.

16. The composition of claim 10 wherein said antibiotic which inhibits DNA gyrase is nalidixic acid.

17. The composition of claim 10 wherein said antibiotic which inhibits DNA gyrase is oxolinic acid.

18. The composition of claim 10 wherein said antibiotic which inhibits DNA gyrase is cinoxacin.

19. The composition of claim 12 wherein said peptide is of the following structure:

$$[KIAGKIA]_3.$$

20. The composition of claim 13 wherein said peptide is of the following structure:

KLASKAGKIAGKIAKVALKAL

21. The composition of claim 11 wherein said magainin peptide is Magainin II.

22. The process of claim 1 wherein each of said peptide or protein and said antibiotic which inhibits DNA gyrase is administered in an amount ineffective in inhibiting growth of a target cell in a host if administered alone to a host.

23. The composition of claim 10 wherein each of said components (a) and (b) are present in an amount ineffective to inhibit growth of a target cell in a host if administered alone to a host.

24. The process of claim 1 wherein the peptide is a PGLa peptide.

25. The process of claim 1 wherein the peptide is a XPF peptide.

26. The process of claim 1 wherein the peptide is a CPF peptide.

27. The process of claim 1 wherein the peptide is a cecropin.

28. The process of claim 1 wherein the peptide is a sarcotoxin.

29. The process of claim 2 wherein said magainin peptide includes the following basic peptide structure:
$-R_{11}-R_{11}-R_{12}-R_{13}-R_{11}-R_{14}-R_{12}-R_{11}-R_{14}-R_{12}-R_{11}-R_{11}-R_{11}-R_{14a}-(R_{15})_n$ $-R_{14a}R_{14}-$, wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ and $R_{14a}$ are hydrophobic or basic hydrophilic amino acids, $R_{15}$ is glutamic acid or aspartic acid, a hydrophobic amino acid, or a basic hydrophilic amino acid, and n is 0 or 1.

30. The process of claim 2 wherein said magainin peptide includes the following basic peptide structure:

$$-R_{14}-R_{11}-R_{14a}-R_{12}-R_{11}-R_{11}-R_{12}-R_{1\text{-}3}-R_{11}-R_{14}-R_{12}-R_{11}-R_{11}-R_{12},$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ and $R_{14a}$ are hydrophobic or basic hydrophilic amino acids.

31. The composition of claim 10 wherein the peptide is a PGLa peptide.
32. The composition of claim 10 wherein the peptide is a XPF peptide.
33. The composition of claim 10 wherein the peptide is a CPF peptide.
34. The composition of claim 10 wherein the peptide is a cecropin.
35. The composition of claim 10 wherein the peptide is a sarcotoxin.
36. The composition of claim 11 wherein said magainin peptide includes the following basic peptide structure:

$$-R_{11}-R_{11}-R_{12}-R_{13}-R_{11}-R_{14}-R_{12}-R_{11}-R_{1\text{-}4}-R_{12}-R_{11}-R_{11}-R_{11}-R_{14a}-(R_{15})_n-R_{14a}-R_{14}-,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ and $R_{14a}$ are hydrophobic or basic hydrophilic amino acids, $R_{15}$ is glutamic acid or aspartic acid, a hydrophobic amino acid, or a basic hydrophilic amino acid, and n is 0 or 1.

37. The composition of claim 11 wherein said magainin peptide includes the following basic peptide structure:

$$-R_{14}-R_{11}-R_{14a}-R_{12}-R_{11}-R_{11}-R_{12}-R_{1\text{-}3}-R_{11}-R_{14}-R_{12}-R_{11}-R_{11}-R_{12}-,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ and $R_{14a}$ are hydrophobic or basic hydrophilic amino acids.

38. A process of inhibiting growth of a microbe in a host, comprising:
administering to a host at least one biologically active amphiphilic peptide selected from the group consisting of:
(a) a magainin peptide;
(b) a PGLa peptide;
(c) an XPF peptide;
(d) a CPF peptide;
(e) a cecropin;
(f) a sarcotoxin;
(g) a basic polypeptide having at least sixteen amino acids, wherein said basic polypeptide includes at least eight hydrophobic amino acids and at least eight hydrophilic amino acids;
(h) a peptide including the following basic structure $X_{40}$:

$$(R_{41}-R_{42}-R_{42}-R_{43}-R_{41}-R_{42}-R_{42})_n,$$

wherein $R_{41}$ is a basic hydrophilic amino acid, $R_{42}$ is a hydrophobic amino acid, $R_{43}$ is a neutral hydrophilic amino acid or hydrophobic amino acid, and n is from 2 to 5; and
(i) a peptide including the following basic structure $X_{50}$:

$$R_{41}-R_{42}-R_{42}-R_{43}-R_{41}-R_{42}-R_{42}-R_{41}-R_{42}-R_{42}-R_{41}-R_{41}-R_{42},$$

wherein $R_{41}$ is a basic hydrophilic amino acid, $R_{42}$ is a hydrophobic amino acid, $R_{43}$ is a neutral hydrophilic amino acid or a hydrophobic amino acid, and an antibiotic which inhibits DNA gyrase, said biologically active amphiphilic peptide and said antibiotic which inhibits DNA gyrase being administered in a combined amount effective to inhibit growth of a microbe in a host.

39. The process of claim 38 wherein the peptide is a magainin peptide.
40. The process of claim 39 wherein said magainin peptide includes the following basic peptide structure:

$$-R_{11}-R_{11}-R_{12}-R_{13}-R_{11}-R_{14}-R_{12}-R_{11}-R_{1\text{-}4}-R_{11}-R_{12}-\quad R_{11}-R_{11}-R_{11}-R_{14a}-(R_{15})_n-R_{14a}-R_{14}-,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ and $R_{14a}$ are hydrophobic or basic hydrophilic amino acids, $R_{15}$ is glutamic acid or aspartic acid, a hydrophobic amino acid, or a basic hydrophilic amino acid, and n is 0 or 1.

41. The process of claim 39 wherein said magainin peptide includes the following basic peptide structure:

$$-R_{14}-R_{11}-R_{14a}-R_{12}-R_{11}-R_{11}-R_{12}-R_{1\text{-}3}-R_{11}-R_{14}-R_{12}-R_{11}-R_{12}-,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, and $R_{14}$ and $R_{14a}$ are hydrophobic or basic hydrophilic amino acids.

42. A composition comprising:
(a) at least one biologically active amphiphilic peptide selected form the group consisting of:
(i) a magnesium peptide;
(ii) a PGLa peptide;
(iii) an XPF peptide;
(iv) a CPF peptide;
(v) a cecropin;
(vi) a sarcotoxin;
(vii) a basic polypeptide having at least sixteen amino acids, wherein said basic polypeptide includes at least eight hydrophobic amino acids and at least eight hydrophilic amino acids;
(viii) a peptide including the following basic structure $X_{40}$:

$$(R_{41}-R_{42}-R_{42}-R_{43}-R_{41}-R_{42}-R_{42})_n,$$

wherein $R_{41}$ is a basic hydrophilic amino acid, $R_{42}$ is a hydrophobic amino acid, $R_{43}$ is a neutral hydrophilic amino acid or a hydrophobic amino acid, and n is from 2 to 5; and
(ix) a peptide which includes the following basic structure $X_{50}$:

$$R_{41}-R_{42}-R_{42}-R_{43}-R_{41}-R_{42}-R_{42}-R_{41}-R_{42}-R_{42}-R_{41}-R_{42},$$

wherein $R_{41}$ is a basic hydrophilic amino acid, $R_{42}$ is a hydrophobic amino acid, $R_{43}$ is a neutral hydrophilic amino acid or a hydrophobic amino acid, and
(b) an antibiotic which inhibits DNA gyrase; and (c) an acceptable pharmaceutical carrier, wherein said components (a) and (b) are present in a combined amount effective to inhibit growth of a microbe in a host.

43. The composition of claim 42 wherein the peptide is a magainin peptide.

44. The composition of claim 43 wherein said magainin peptide includes the following basic peptide structure:

—$R_{11}$—$R_{11}$—$R_{12}$—$R_{13}$—$R_{11}$—$R_{14}$—$R_{12}$—$R_{11}$—$R_{14}$—$R_{11}$—$R_{12}$— $R_{11}$—$R_{11}$—$R_{11}$—$R_{14a}$—($R_{15}$)$_n$—$R_{14a}$—$R_{14}$—, wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ and $R_{14a}$ are hydrophobic or basic hydrophilic amino acids, $R_{15}$ is glutamic acid or aspartic acid, a hydrophobic amino acid, or a basic hydrophilic amino acid, and n is 0 or 1.

45. The composition of claim 43 wherein said magainin peptide includes the following basic peptide structure:

—$R_{14}$—$R_{11}$—$R_{14a}$—$R_{12}$—$R_{11}$—$R_{11}$—$R_{12}$—$R_{13}$—$R_{11}$— $R_{14}$—$R_{12}$—$R_{11}$—$R_{11}$—$R_{12}$—, wherein $R_{11}$ is a hydrophobic amino acid, $R_{12}$ is a basic hydrophilic amino acid, $R_{13}$ is a hydrophobic, neutral hydrophilic, or basic hydrophilic amino acid, and $R_{14}$ and $R_{14a}$ are hydrophobic or basic hydrophilic amino acids.

46. The process of claim 1 wherein the microbe is a bacterium.

47. The process of claim 1 wherein said at least one biologically active peptide or protein is administered topically.

48. The process of claim 1 wherein said at least one biologically active peptide or protein is administered systemically.

49. The process of claim 1 wherein said antibiotic which inhibits DNA gyrase is administered topically.

50. The process of claim 1 wherein said antibiotic which inhibits DNA gyrase is administered systemically.

51. The process of claim 1 wherein said at least one biologically active peptide or protein and said antibiotic which inhibits DNA gyrate are administered topically.

52. The process of claim 1 wherein said at least one biologically active peptide or protein and said antibiotic which inhibits DNA gyrase are administered systemically.

53. The process of claim 38 wherein the microbe is a bacterium.

54. The process of claim 38 wherein said antibiotic which inhibits DNA gyrase is a quinolone antibiotic.

55. The process of claim 54 wherein said quinolone antibiotic is ciprofloxacin.

56. The process of claim 38 wherein said antibiotic which inhibits DNA gyrase is nalidixic acid.

57. The process of claim 38 wherein said antibiotic which inhibits DNA gyrase is oxolinic acid.

58. The process of claim 38 wherein said antibiotic which inhibits DNA gyrase is cinoxacin.

59. The composition of claim 42 wherein said antibiotic which inhibits DNA gyrase is a quinolone antibiotic.

60. The composition of claim 59 wherein said quinolone antibiotic is ciprofloxacin.

61. The composition of claim 42 wherein said antibiotic which inhibits DNA gyrase is nalidixic acid.

62. The composition of claim 42 wherein said antibiotic which inhibits DNA gyrase is oxolinic acid.

63. The composition of claim 42 wherein said antibiotic which inhibits DNA gyrase is cinoxacin.

* * * * *